(12) United States Patent
Lindemann et al.

(10) Patent No.: US 7,288,094 B2
(45) Date of Patent: Oct. 30, 2007

(54) SYSTEM AND METHOD FOR RETAINING SCREWS RELATIVE TO A VERTEBRAL PLATE

(75) Inventors: Gary S. Lindemann, Collierville, TN (US); Wilder Companioni, Cordova, TN (US)

(73) Assignee: SDGI Holdings, Inc., Wilmington, DE (US)

( * ) Notice: Subject to any disclaimer, the term of this patent is extended or adjusted under 35 U.S.C. 154(b) by 151 days.

(21) Appl. No.: 11/150,564

(22) Filed: Jun. 10, 2005

(65) Prior Publication Data

US 2006/0293669 A1    Dec. 28, 2006

(51) Int. Cl.
*A61B 17/56* (2006.01)
(52) U.S. Cl. .......................... 606/61; 606/69
(58) Field of Classification Search .......... 606/61, 606/69, 70–71
See application file for complete search history.

(56) References Cited

U.S. PATENT DOCUMENTS

| | | | |
|---|---|---|---|
| 5,578,034 A | 11/1996 | Estes | |
| 5,876,402 A | 3/1999 | Errico et al. | |
| 5,931,838 A | 8/1999 | Vito | |
| 6,030,389 A | 2/2000 | Wagner et al. | |
| 6,193,721 B1 * | 2/2001 | Michelson | 606/70 |
| 6,258,089 B1 | 7/2001 | Campbell et al. | |
| 6,331,179 B1 | 12/2001 | Freid et al. | |
| 6,383,186 B1 | 5/2002 | Michelson | |
| 6,398,783 B1 | 6/2002 | Campbell et al. | |
| 6,428,542 B1 | 8/2002 | Michelson | |
| 6,454,771 B1 | 9/2002 | Michelson | |
| 6,527,776 B1 | 3/2003 | Michelson | |
| 6,602,255 B1 | 8/2003 | Campbell et al. | |
| 6,626,907 B2 | 9/2003 | Campbell et al. | |
| 6,695,846 B2 | 2/2004 | Richelsoph et al. | |
| 6,793,658 B2 * | 9/2004 | LeHuec et al. | 606/61 |
| 2002/0188296 A1 * | 12/2002 | Michelson | 606/71 |
| 2003/0040749 A1 | 2/2003 | Grabowski et al. | |
| 2003/0093082 A1 | 5/2003 | Campbell et al. | |
| 2004/0034352 A1 | 2/2004 | Needham et al. | |
| 2004/0127904 A1 * | 7/2004 | Konieczynski et al. | 606/70 |
| 2005/0075633 A1 * | 4/2005 | Ross | 606/61 |
| 2005/0283152 A1 * | 12/2005 | Lindemann et al. | 606/61 |

* cited by examiner

*Primary Examiner*—Eduardo C. Robert
*Assistant Examiner*—Anitza M San Miguel
(74) *Attorney, Agent, or Firm*—Coats & Bennett, P.L.L.C.

(57) ABSTRACT

Devices and methods for maintaining the position of a screw relative to a vertebral plate. The device includes a plate having one or more screw holes each sized to receive a screw for attaching the plate to the vertebral member(s). A cap may be movably coupled to the plate. In one position the cap may overlap into the screw hole for receiving the bone screw. The bone screw may be inserted into the screw hole and mounted into the bone with the cap overlapping into the screw hole. In one embodiment the screw moves past the cap and may be captured beyond the cap preventing back-out of the screw. The cap may also be moved to a second position to allow for removal of the bone screw from the vertebral member.

21 Claims, 7 Drawing Sheets

SYSTEM AND METHOD FOR RETAINING SCREWS RELATIVE TO A VERTEBRAL PLATE

BACKGROUND

The human spine is a biomechanical structure consisting of thirty-three vertebral members and is responsible for protecting the spinal cord, nerve roots and internal organs of the thorax and abdomen. The spine also provides structural support for the body while permitting flexibility of motion. In certain surgical procedures it is necessary to secure together two or more of the vertebral members. The procedure may be necessary for example as a result of physical trauma or degenerative diseases.

One type of surgical procedure includes attachment of a vertebral plate to the vertebral members. The vertebral plate is sized to extend across two or more of the vertebral members. One or more bone screws extend through screw holes in the plate and into the vertebral members to secure the plate. One issue with the attachment is that the screws may tend to loosen and back-out of the vertebral members. Screw retention devices may be necessary to prevent the screw from backing-out of the vertebral members. While a variety of anti-backout approaches have been proposed, there remains a need for alternative designs.

SUMMARY

The present application is directed to embodiments for a zero-step system for maintaining the position of a screw relative to a vertebral plate. The system may be zero-step, meaning that no elements are actively moved by a surgeon on or about the plate to retain the screw within a screw hole in the plate.

In one embodiment, a cap is movably coupled to the plate. In a first position, at least a portion of the cap overlaps into the screw hole. With the cap in the first position, the screw may be inserted into the screw hole and mounted into the vertebral member with a head of the screw being captured by the cap thus preventing back-out of the screw. Removal of the screw from the vertebral member requires that the cap be moved to a second position. The second position does not interfere with the screw allowing for removal from the vertebral member and the plate.

DETAILED DESCRIPTION

The present invention is directed to embodiments for a system for preventing a screw from backing-out relative to a vertebral plate. The system is not required to be moved before, during or after insertion of the screw to retain the screw. In the embodiments described in more detail below, a cap 30 is coupled to the plate 20 and disposed in a retention position overlapping into a screw hole 21 in the plate 20. The screw 70 is inserted into the screw hole 21 and into the vertebral member with the cap 30 in the overlapping position. Subsequently, the cap 30 may be movable to a release position to permit removal of the screw 70. The release position may be clear of the screw hole 21, or may still extend into the screw hole but not enough to prevent removal of the screw 70.

Figure 1:
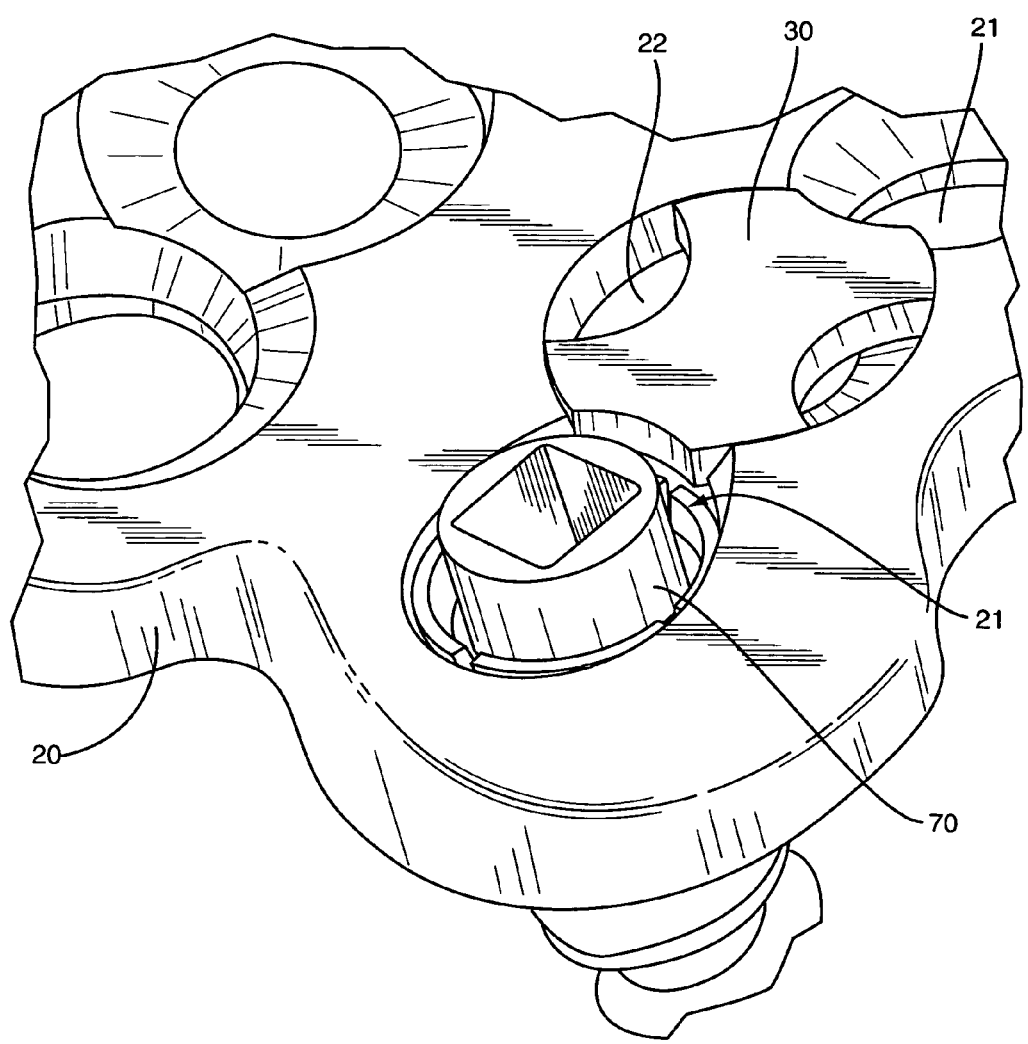
FIG. 1 is a partial perspective view of the plate having a cap the prevents screw back out according to one embodiment of the present invention.

FIG. 1 illustrates one embodiment having a vertebral plate, shown generally as 20, with one or more screw holes 21. A cap 30 is operatively coupled to the plate 20 and is movable from a retention position in which the cap 30 partially overlaps a screw hole 21 to a release position. A screw 70 is inserted into the screw hole 21 to secure the plate 20 to the vertebral member. As the screw 70 is inserted into the screw hole 21, the cap 30 engages a portion of the screw 70 to deflect the portion inwardly so that the screw's effective size is less than original size. After insertion has progressed where the screw 70 is beyond the cap 30, the deflected portion of the screw 70 rebounds back outward to extend under the cap 30 which prevents the screw from backing out.

One form of vertebral fixation utilizes a plate 20 and screws 70 to connect together one or more vertebral members. The plate 20 includes a first surface that is positioned towards the vertebral members, and a second surface that faces away from the vertebral members. The plate 20 may be sized to extend across a single vertebral member, or a number of vertebral members. Additionally, the plate 20 may have both a medial and lordotic curve to conform to the dimensions of the vertebral members. One or more screw holes 21 extend through the plate 20 and are each sized to receive a screw 70. The screw holes 21 may have a variety of sizes and orientations depending upon the specific application. The screw holes may have a larger size 29 at the second surface and a smaller size at the first surface. In use, the plate 20 is positioned on the exterior of the vertebral members with the first surface facing towards the vertebral members. Screws 70 extend through the screw holes 21 and engage the vertebral members to hold the plate 20 in position.

Figure 2:
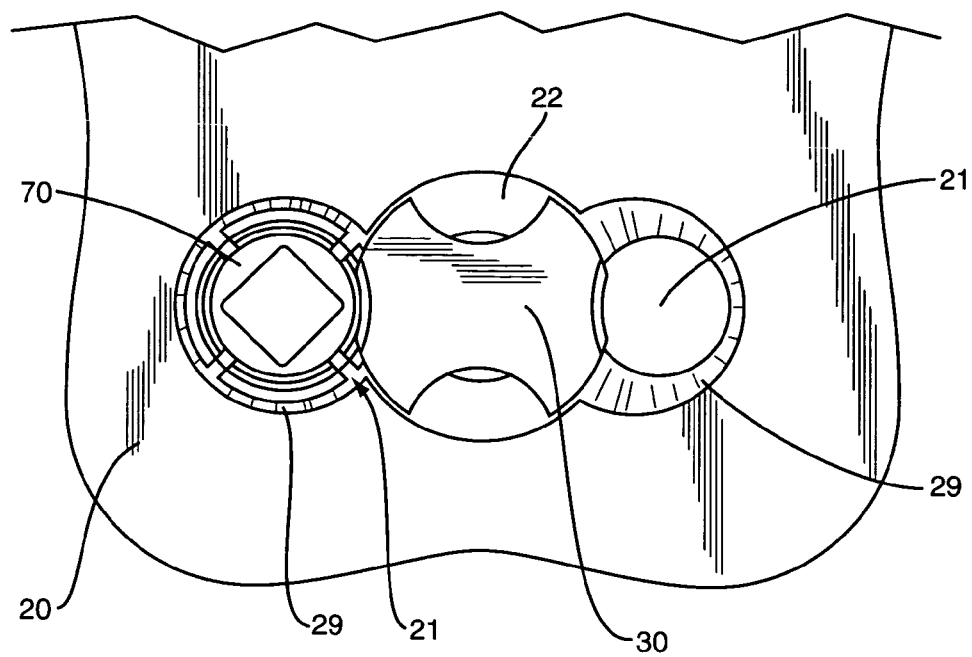
FIG. 2 is a top view of the cap in a retention position according to one embodiment of the present invention.
Figure 3:
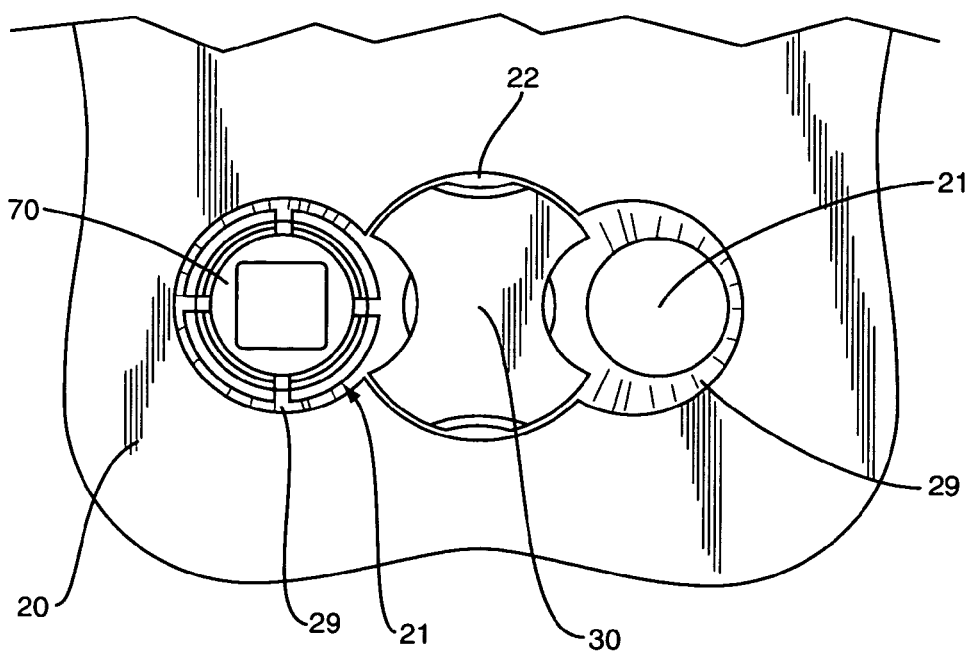
FIG. 3 is a top view of the cap in a release position according to one embodiment of the present invention.

The cap 30 is coupled to the plate 20 and movable between first and second positions. In one embodiment, cap 30 is positionable relative to the plate 20 between a retention position and a release position. In the retention position as illustrated in FIG. 2, the cap 30 extends outwardly into or over the screw hole 21. In the release position as illustrated in FIG. 3, the cap 30 is rotated away from the screw hole 21. The cap 30 may be clear of the screw hole 21, or moved enough to not interfere with removal of the screw 70 from the hole 21. The embodiments of FIGS. 2 and 3 illustrate a screw 70 positioned in the left screw hole 21, with the right screw hole being open (i.e., without a screw 70).

A variety of means may be used for movably coupling the cap 30 to the plate 20, including for example, interference fit, snap fit, staking, and swaging. The cap 30 may also be attached via a removable or non-removable fastener, such as screw, rivet, and the like. In one embodiment, the cap 30 may be threaded and mate with corresponding threads on the plate 20. Movement of the cap 30 between the retention and release positions may occur by rotation of the cap 30, a sliding movement of the cap 30, and other like movements.

Figure 4:
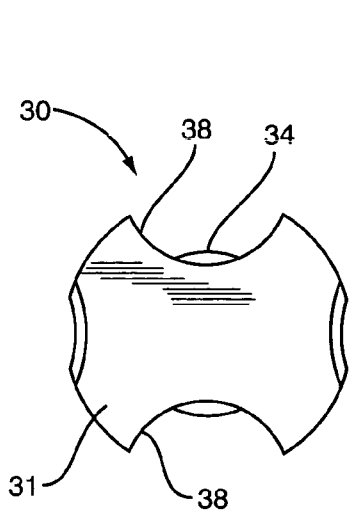
FIG. 4 is a top view of a cap according to one embodiment of the present invention.
Figure 5:
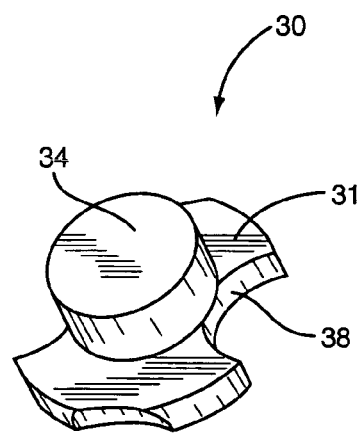
FIG. 5 is a bottom perspective view of the cap according to one embodiment of the present invention.

The cap 30 includes a flange 31 and an outwardly extending plug 34 as illustrated in FIGS. 4 and 5. The flange 31 may have a shape that conforms to the adjacent screw holes 21 when the cap 30 is in the release position. For example, the cap flange 31 may have scalloped edges 38 that conform to the outer circumferences of the screw hole 21. Therefore, in the release position, the flange 31 does not extend into the screw hole 21, allowing removal of the screw 70 without deflection of the screw 70.

In some embodiments, the cap 30 may rest in a corresponding cavity 22 in the bone plate 20. The cavity 22 is located proximate the screw hole(s) 21, and advantageously is of sufficient depth to allow a top surface of the cap 30 to be flush with the top surface of the plate 20.

Figure 6:
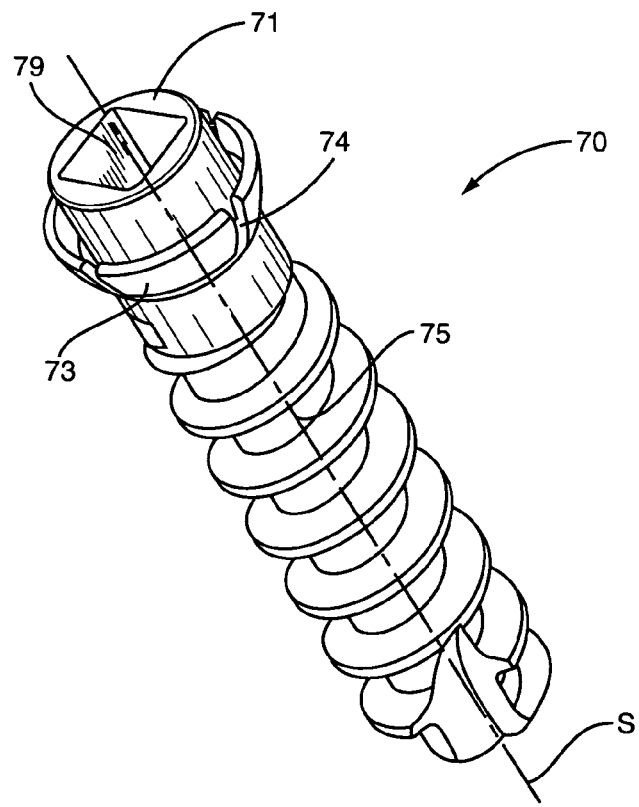
FIG. 6 is a perspective view of a screw according to one embodiment of the present invention.

The screw 70 functions primarily to secure the plate 20 to the vertebral members. One embodiment of a screw 70 is illustrated in FIG. 6 and includes a head 71, a flange 73, and a shaft 75. The head 71 may include a receiving opening 79 configured to receive a tool for the translation of rotational force from the tool to drive the screw 70 into the vertebral member. This may be achieved by a variety of means well known in the art. The shaft 75 is threaded in a conventional manner to pull the screw 70 into the vertebral member and to anchor the screw 70 into the vertebral member. The flange 73 is disposed proximate to the head 71 and is deflectable during insertion to pass beyond and extend under the cap 30 so as to prevent the screw 70 from backing out. The flange 73 may be normally angled upwardly and outwardly from the longitudinal axis S. Thus the flange 73 normally has a maximum width at a distal end at or near the head 71 and a minimum width at the shaft 75.

The flange 73 is deflectable inwardly toward the longitudinal axis S during insertion of the screw 70. The deflection results in the effective size being less than an original size. Typically this occurs as the flange 73 passes the cap 30 during screw insertion. After passing beyond the cap 30, the flange 73 rebounds outward towards the original size to extend under the cap 30 so that the cap 30 extends over or overlaps the flange 73 so as to prevent the screw 70 from backing-out. Advantageously the flange 73 fully rebounds to the original size after passing beyond the cap 30, however this is not required.

In one embodiment the flange 73 may be segmented by a plurality of slits 74 forming flange segments. In such embodiments the flanges segments may be independently and or sequentially deflectable as the screw 70 rotates during insertion of the screw 70. Thus, the deflection may be isolated to the flange segment that is in contact with the cap 30 during insertion. The remaining flange segments may remain in their undeflected state. Further, it has been determined that smaller flange segments deflect more readily than larger flange segments. In the embodiment of FIG. 6, a total of four flange segments are included. Various numbers of flange segments may be used and are contemplated by different embodiments. In one embodiment, the flange 73 is continuous (i.e., one flange 73 having no slits 74).

Figure 7A:
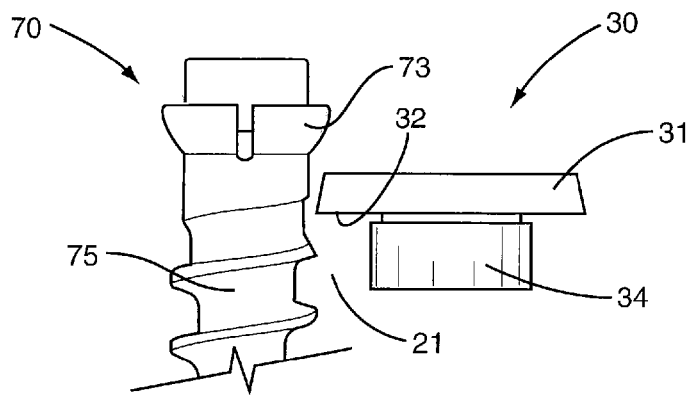
FIGS. 7A, 7B, and 7C are schematic views illustrating a screw being moved relative to a cap according to one embodiment of the present invention.
Figure 7B:
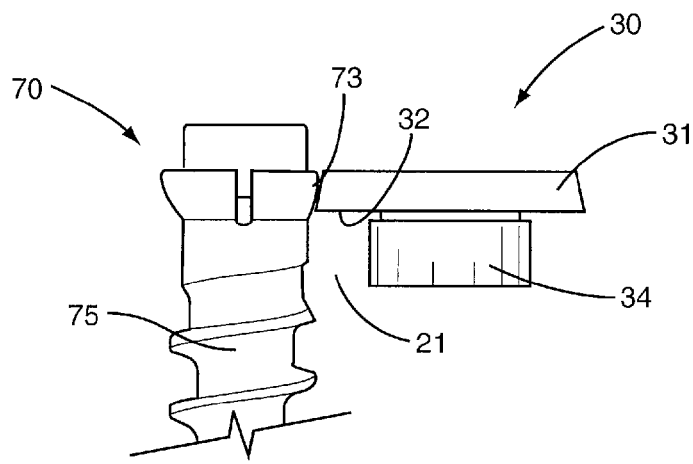
Figure 7C:
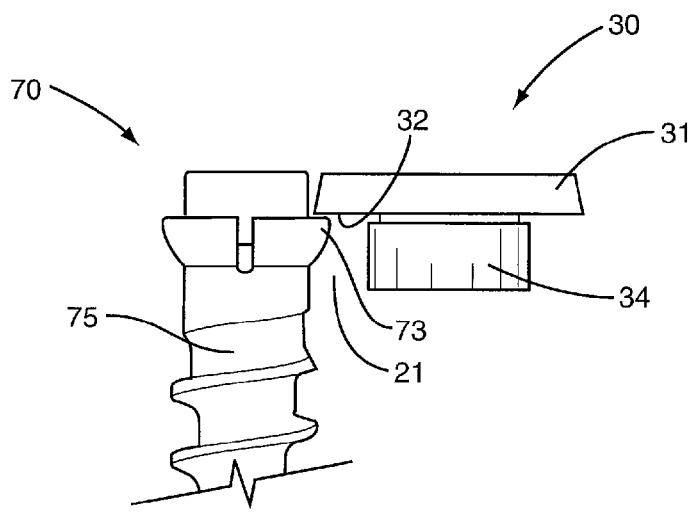

The movement of the screw 70 during insertion past the cap 30 is illustrated in FIGS. 7A, 7B, and 7C. Cap 30 is positioned in the retention position and partially overlaps the screw hole 21. The screw 70 is inserted into the screw hole 21 while the cap 30 is in the retention position as illustrated in FIG. 7A. As the screw 70 is rotated, the threaded shaft 75 pulls the screw 70 into the vertebral member and anchors the plate 20. As the screw 70 is inserted, the flange 73 contacts the cap 30 as illustrated in FIG. 7B. The cap 30 deflects the screw flange 73 inwardly thereby reducing the effective overall size of the flange. This reduction in the flange size allows the screw 70 to pass by the cap 30. After insertion has progressed where the screw flange 73 is beyond the cap 30, the screw flange 73 rebounds towards the original size and extends under the cap 30 as illustrated in FIG. 7C. The flange 73 may expand outward to the original size, or may have a smaller size than original. In the event the screw 70 begins to back out, the flange 73 contacts the bottom surface 32 of the cap 30. Since the flange 73 is unable to deflect in this direction, the cap 30 prevents the screw 70 from backing out.

Figure 8:
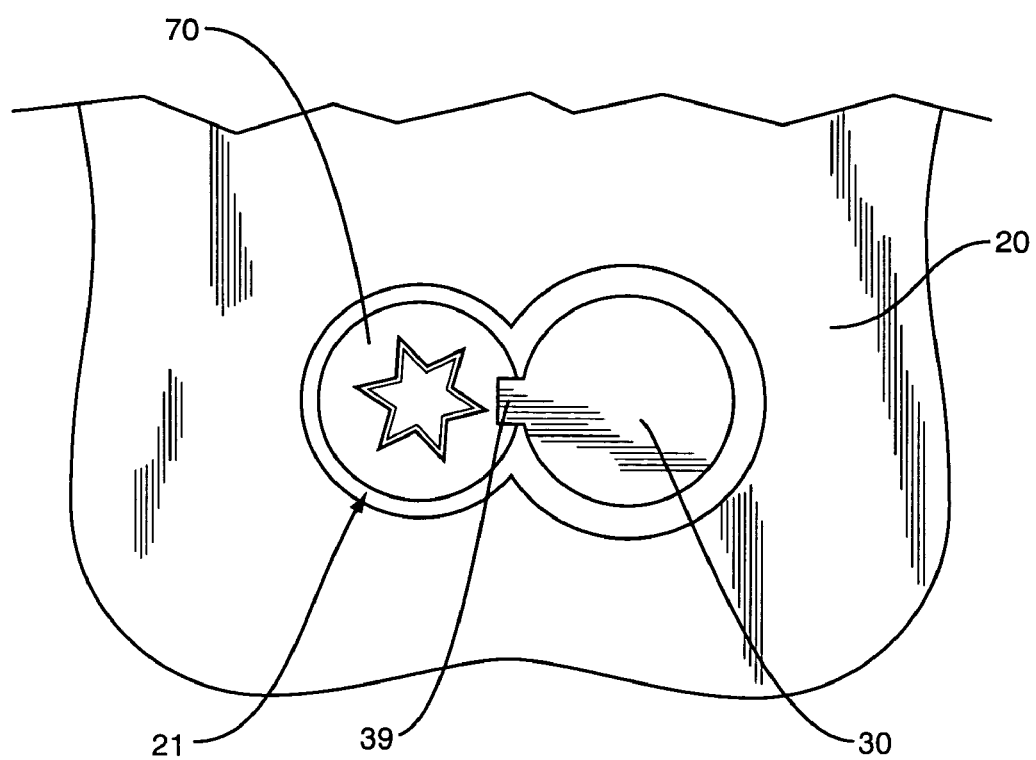
FIG. 8 is a top view of a plate and cap according to one embodiment of the present invention.

The embodiments illustrated in FIGS. 1-3 illustrate designs where the cap 30 may extend outwardly into or over one or more screw holes 21 to prevent the back-out of more than one screw 70. In these embodiments the cap 30 may advantageously be moved to a release position to permit the removal of the corresponding screws 70. FIG. 8 illustrates another embodiment with the cap 30 locking only a single screw hole 21. Cap 30 comprises an extension 39 that extends into the screw hole 21. Cap 30 is rotatable relative to the plate 20 and can be moved to a release position with the extension 39 moved away from the screw hole 21. This release position allows for removing the screw 70 from the vertebral member.

Figure 9:
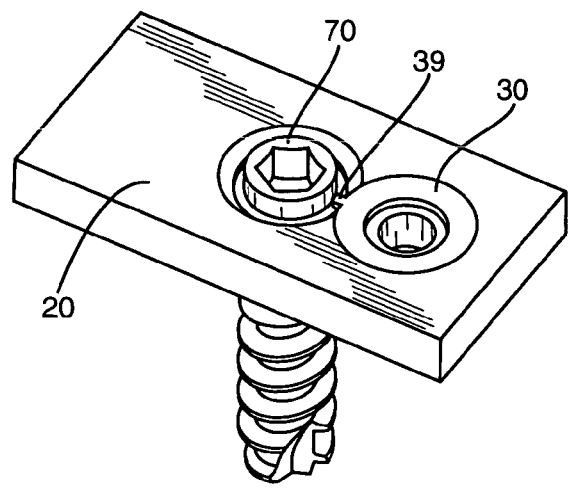
FIG. 9 is a perspective view of a cap that prevents screw back out according to one embodiment of the present invention.

Another embodiment to prevent back out of the screw 70 is illustrated in FIG. 9. This embodiment features the cap 30 interacting with the screw 70 during insertion of the screw 70 into the vertebral member. The cap 30 engages the screw 70 and prevents back out from the plate 20.

The cap 30 includes an extension 39 that overlaps into the screw hole 21 when the cap 30 is in the retention position. The cap 30 is movably secured to the plate 20 in the some manner as described above. In a release position, the cap 30 is moved such that the extension 39 does not interfere with the removal of the screw 70.

Figure 10:
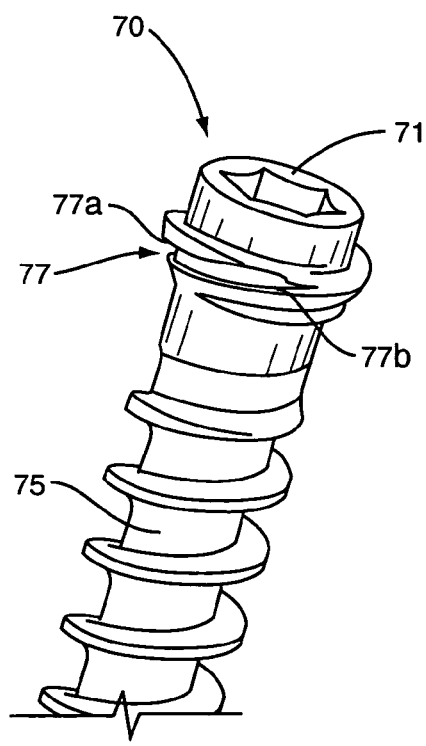
FIG. 10 is partial perspective view of a screw according to one embodiment of the present invention.

Screw 70 includes a head 71 and shaft 75 as illustrated in FIG. 10. Screw 70 further includes a thread 77 that receives the extension 39. In the embodiment of FIG. 10, thread 77 includes an upper surface 77a and a lower surface 77b. Depending upon the application, thread 77 may be positioned on the head 71, shaft 75, or both to engage the extension 39. In the embodiment of FIG. 10, thread 77 is positioned on the head 71 with the distance between the surfaces 77a, 77b forming a channel that receives the extension 39. In one embodiment, thread 77 has the same pitch as the threaded shaft 75. Thread 77 may include more than one thread, such as a double thread or triple thread. This allows for the extension 39 to feed into the thread within a predetermined amount of rotation. By way of example, a double thread provides that the extension feed into the thread 77 within 180° of rotation, and a triple thread provides feed within 120° of rotation.

During rotation and insertion of the screw 70 into the vertebral member, the shaft 75 bites into the vertebral member to a depth where the thread 77 engages the extension 39. In one embodiment, the pitch of the thread 77 flattens as it nears the top of the head 71. When the screw has been rotated to a predetermined position, extension 39 rides onto the flattened surface adjacent to the screw head 71. Extension 39 extends over a section of the head 71 to prevent screw back out. In this embodiment, extension 39 may apply a compressive force to the screw to further prevent back out.

In one embodiment, thread 77 includes a deformable section. Initially, the deformable section allows for the extension 39 to ride along the thread 77. Movement of the extension 39 deforms the deformable section and locks the extension in position along the thread 77. This prevents the screw 70 from backing out of the plate 20. In another embodiment, a spring-biased protrusion is positioned along the thread 77. The extension 39 biases the protrusion inward during insertion of the screw 70. After passage, the protrusion springs back outward and blocks the thread 77 thus preventing back-out.

In the embodiments discussed above, engagement between the cap 30 and screw 70 may cause a snapping action as the screw 70 passes beyond the cap 30. This action may be tactilely detected by the surgeon and provide tactile assurance that the cap 30 is engaging the screw 70. In another embodiment the surgeon may visually confirm the relative positions of the cap 30 and screw 70. In one embodiment the cap 30 and screw 70 are contrastingly colored to ease the visual confirmation by the surgeon that the cap 30 is seated over the screw 70.

Figure 11:
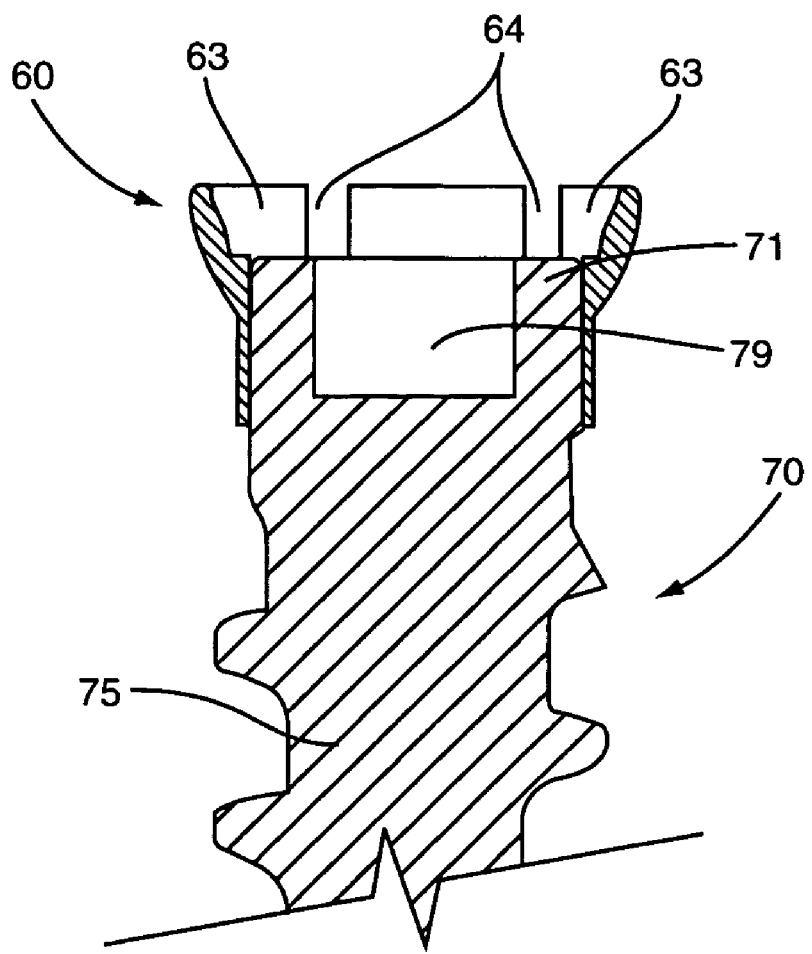
FIG. 11 is side view of an attachment connected to a screw according to one embodiment of the present invention.

In the embodiments discussed above, the screw 70 may be deflected as it contacts the cap 30. In one embodiment, the screw 70 is constructed of a deflectable material that deflects during contact with the cap 30 and then expands back towards the original shape and size after the contact. In another embodiment such as illustrated in FIG. 11, an attachment 60 is attached to the screw head 71. Attachment 60 is constructed of a deflectable material that deflects during contact with the cap 30. The attachment 60 is positioned to contact the cap 30 and is constructed of a material that deflects during the contact. The screw 70 may not actually contact the cap 30 and may be constructed of a more rigid material. The attachment 60 is securely fastened to the screw 70 such that screw is prevented from back out by the attachment 60. The embodiment of FIG. 11 illustrates an embodiment similar to that of FIG. 6 with slots 64 forming flanges 63 that are deflected by contact with the cap 30. The attachment 60 may also have other shapes, such as the embodiment disclosed in FIG. 10.

In the embodiments described above, screw 70 (or attachment 60) is deflected as the cap 30 remains undeflected. In another embodiment, the screw 70 is constructed of a rigid material that deflects the cap 30 during insertion of the screw 70. Using FIGS. 9 and 10 as an example, extension 39 is deflected as it rides within the thread 77. The extension 39 then expands towards the original position and into the indent 77b to prevent screw back out. In another embodiment, deflection occurs between both the screw 70 (and attachment 60) and the cap 30.

The term vertebral member is used generally to describe the vertebral geometry comprising the vertebral body, pedicles, lamina, and processes. The device may be sized and shaped, and have adequate strength requirements to be used within the different regions of the vertebra including the cervical, thoracic, and lumbar regions.

The retaining system has been discussed in the context of a vertebral plate, however, the system is also applicable to other applications in the body using plates and attachment screws.

A variety of screws 70 may be used in these embodiments, such as a fixed angle screw and a variable angle screws. Fixed angle screws do not pivot or translate relative to the plate 20 and an axis of the aperture 21. Variable angle screws can be angled relative to the plate 20 and to an axis of the aperture 21. The degree of angulation can vary depending upon the application. Further, the variable angle screw can be delivered at a variety of angles relative to the axis of the aperture 21. Embodiments of fixed angle and variable angle screws are disclosed in U.S. Pat. No. 6,669,700, and are herein incorporated by reference in their entirety.

The present invention may be carried out in other specific ways than those herein set forth without departing from the scope and essential characteristics of the invention. Advantageously the cap 30 is mounted on the plate 20 and oriented in the retention position during factory assembly. The retaining system may also be used with polyaxial screws. The present embodiments are, therefore, to be considered in all respects as illustrative and not restrictive, and all changes coming within the meaning and equivalency range of the appended claims are intended to be embraced therein.

What is claimed is:

1. A method of retaining a screw in a vertebral plate, the method comprising the steps of:
    moving a cap attached to the vertebral plate to a first position to overlap a screw hole in the vertebral plate;
    inserting a screw into the screw hole;
    contacting the screw with the cap as the screw is inserted into the vertebral member;
    deflecting at least one of the cap and the screw to a reduced size as the screw moves past the cap;
    expanding the at least one of the cap and screw that was deflected from the reduced size towards an original size after the screw has past beyond the cap; and
    moving the cap to a second position that is still attached to the plate and removing the screw from the screw hole without the screw contacting the cap.

2. The method of claim 1, wherein the step of deflecting one or both of the cap and the screw to the reduced size as the screw is moved past the cap comprises deflecting a flange segment that extends around a limited periphery of a head of the screw.

3. The method of claim 1, wherein the step of deflecting one or both of the cap and the screw to the reduced size as the screw is moved past the cap comprises deflecting an attachment that is attached to the screw.

4. The method of claim 1, wherein the step of moving the cap to the second position and removing the screw from the screw hole without the screw contacting the cap comprises rotating the cap to a position away from the screw hole.

5. The method of claim 1, wherein the step of expanding the deflected cap and screw from the reduced size towards the original size after the screw has past beyond the cap comprises positioning a section of the cap beyond a deformable section on the screw.

6. The method of claim 1, further comprising positioning the cap and retaining the first and a second screw simultaneously in the vertebral plate.

7. A method of retaining a screw in a vertebral plate, the method comprising the steps of:
    inserting the screw into a screw hole in the plate;
    contacting a cap that extends into the screw hole with the screw as the screw moves through the screw hole and thereby deflecting the screw to a reduced size by contact with the cap;

moving the screw beyond the cap and causing the screw to expand from the reduced size towards an original size underneath the cap;

maintaining the cap attached to the plate and moving the cap to a second position; and removing the screw from the vertebral plate without the screw contacting the cap.

8. The method of claim 7, wherein the step of deflecting the screw to the reduced size by contact with the cap comprises deflecting a flange segment of the screw.

9. The method of claim 7, wherein the step of deflecting the screw to the reduced size by contact with the cap comprises deflecting an attachment that is connected to the screw.

10. The method of claim 7, wherein the step of moving the cap to the second position comprises rotating the cap from a first position that partially extends into the screw hole to the second position that is clear of the screw hole.

11. The method of claim 7, further comprising deflecting the screw through contact with an extension of the cap that is positioned into the screw hole.

12. The method of claim 7, further comprising moving an extension on the cap along a thread on a head of the cap.

13. The method of claim 7, further comprising sequentially deflecting segment portions of the screw as the screw is being inserted into the screw hole.

14. A method of retaining a screw in a vertebral plate, the method comprising the steps of:

inserting the screw into a screw hole in the plate;

contacting a cap that extends into the screw hole with the screw as the screw moves through the screw hole;

moving the screw through the screw hole and deflecting the cap to a reduced size by contact with the screw;

moving the screw beyond the cap and causing the cap to expand into the screw hole from the reduced size towards an original size;

maintaining the cap attached to the plate and moving the cap to a second position clear of the screw hole; and removing the screw from the vertebral plate without the screw contacting the cap.

15. A plate system for contacting at least two vertebral members, the system comprising:

a plate having a length to overlap portions of at least two adjacent vertebral members, the plate having an upper surface that faces away from the vertebral members and a lower surface that faces towards the vertebral members;

a screw hole extending through the plate from the upper surface through the lower surface, the screw hole having a width;

a screw having a central longitudinal axis and adapted to engage one of the vertebral members, the screw having a shaft for insertion into the vertebral member and a head; and a locking element adapted to prevent the screw that is inserted into the screw hole from backing out of the screw hole, the locking element being attached to the plate and movable between a first position that extends into the screw hole to reduce the width of the screw hole, and a second position that is away from the screw hole, the locking element being in the first position during insertion of the screw and being constructed of a rigid material causing the screw to deflect during the insertion of the screw into the screw hole and extending over at least a portion of the screw upon insertion to prevent the screw from backing out of the plate, the locking element being in the second position during removal of the screw from the vertebral member and positioned away from the screw hole to allow screw removal without deflecting the screw.

16. The device of claim 15, wherein the locking element comprises a scalloped edge that is aligned with the screw hole in the second position to not overlap into the screw hole.

17. The device of claim 15, wherein the screw comprises a thread that mates with an extension that extends outward from the locking element.

18. The device of claim 15, wherein the screw is deflectable in a radial direction towards the longitudinal axis of the screw.

19. The device of claim 15, further comprising an attachment connected to the head of the screw, the attachment deflecting during contact with the locking element.

20. The device of claim 15, further comprising flange segments that extend along a periphery of the screw head, the segments extending outward from the longitudinal axis of the screw and being formed by a plurality of slots.

21. A plate system for contacting at least two vertebral members, the system comprising:

a plate having a length to overlap portions of at least two adjacent vertebral members, the plate having an upper surface that faces away from the vertebral members and a lower surface that faces towards the vertebral members;

a screw hole extending through the plate from the upper surface through the lower surface, the screw hole having a width;

a screw having a central longitudinal axis and adapted to engage one of the vertebral members, the screw having a shaft for insertion into the vertebral member and a head; and a locking element adapted to prevent the screw that is inserted into the screw hole from backing out of the screw hole, the locking element being attached to the plate and movable between a first position that extends into the screw hole to reduce the width of the screw hole, and a second position that is away from the screw hole, the locking element in the first position during insertion of the screw and being constructed of a deflectable material causing the locking element to deflect during the insertion of the screw into the screw hole and rebounding over at least a portion of the screw hole upon screw insertion to prevent the screw from backing out of the plate, the locking element being positioned in the second position during removal of the screw from the vertebral member and being positioned away from the screw hole to allow screw removal without deflecting the locking element.

* * * * *